(12) United States Patent
Totani et al.

(10) Patent No.: US 9,926,522 B2
(45) Date of Patent: Mar. 27, 2018

(54) CULTURE CONTAINER FOR ADHERENT CELLS AND METHOD FOR PRODUCING CULTURE CONTAINER FOR ADHERENT CELLS

(71) Applicant: Toyo Seikan Kaisha, Ltd., Tokyo (JP)

(72) Inventors: Takahiko Totani, Kanagawa (JP); Yoichi Ishizaki, Kanagawa (JP); Satoshi Tanaka, Kanagawa (JP); Ryo Suenaga, Kanagawa (JP); Kyohei Ota, Kanagawa (JP); Masahiro Kuninori, Kanagawa (JP)

(73) Assignee: Toyo Seikan Kaisha, Ltd., Tokyo (JP)

(*) Notice: Subject to any disclaimer, the term of this patent is extended or adjusted under 35 U.S.C. 154(b) by 62 days.

(21) Appl. No.: 13/862,966

(22) Filed: Apr. 15, 2013

(65) Prior Publication Data

US 2013/0230914 A1 Sep. 5, 2013

Related U.S. Application Data

(63) Continuation of application No. PCT/JP2011/005590, filed on Oct. 4, 2011.

(30) Foreign Application Priority Data

Oct. 13, 2010 (JP) ................................. 2010-230543

(51) Int. Cl.
*C12M 1/00* (2006.01)
*C12M 1/12* (2006.01)

(52) U.S. Cl.
CPC ............ *C12M 21/00* (2013.01); *C12M 23/14* (2013.01); *C12M 23/20* (2013.01); *C12M 25/14* (2013.01)

(58) Field of Classification Search
CPC ...... C12M 23/14; C12M 21/00; C12M 25/14; C12M 23/20
See application file for complete search history.

(56) References Cited

U.S. PATENT DOCUMENTS

2004/0096476 A1* 5/2004 Uhrich et al. ....... A61K 9/0024
424/426
2006/0240458 A1* 10/2006 Steichen et al. .................. 435/6
(Continued)

FOREIGN PATENT DOCUMENTS

CN 101652660 A 2/2010
EP 1921450 A1 5/2008
(Continued)

OTHER PUBLICATIONS

Office Action in corresponding Japanese Application No. 2010-230543 dated Nov. 25, 2014 (6 pages).
(Continued)

*Primary Examiner* — Gautam Prakash
(74) *Attorney, Agent, or Firm* — Osha Liang LLP

(57) ABSTRACT

A culture bag for culturing adherent cells is provided without requiring a highly clean production environment and a complex production step such as a masking step. An adherent cell culture vessel that is formed of a polyolefin is configured so that part or the entirety of the inner surface of the culture vessel has a static water contact angle of 95° or more, and has an advancing contact angle and a receding contact angle that satisfy the inequality "advancing contact angle−receding contact angle>25°" when water runs down along the inner surface.

1 Claim, 6 Drawing Sheets

PHENOL-BASED ANTIOXIDANT

(56) References Cited

U.S. PATENT DOCUMENTS

2009/0197333 A1* 8/2009 Saito et al. .................. 435/377
2010/0047845 A1 2/2010 Woodside et al.

FOREIGN PATENT DOCUMENTS

| | | |
|---|---|---|
| JP | 3-187853 A | 8/1991 |
| JP | 6-098756 A | 4/1994 |
| JP | 2006-204232 A | 8/2006 |
| JP | 2008-048654 A | 3/2008 |
| JP | 2008-174714 A | 7/2008 |
| JP | 2009-027944 A | 2/2009 |
| JP | 2009-027945 A | 2/2009 |
| WO | 2006/107843 A1 | 10/2006 |

OTHER PUBLICATIONS

Notification of Transmittal of Translation of the International Preliminary Report on Patentability issued in corresponding International Application No. PCT/JP2011/005590 dated May 16, 2013 (1 page).

International Preliminary Report on Patentability and Written Opinion issued in corresponding International Application No. PCT/JP2011/005590 dated May 8, 2013 (5 pages).

Lu et al., "A Comparative Study of the Wettability of Steel, Carbon, and Polyethylene Fibers by Water," Cement and Concrete Research, vol. 28, No. 6, pp. 783-786, Apr. 10, 1998 (4 pages).

Wang et al.; "Three-dimensional Shape of C6 Glioma Cells on the Fractal Surface"; Chinese Journal of Biomedical Engineering, vol. 28, No. 2, pp. 280-284; Apr. 2009 (5 pages).

International Search Report issued in corresponding International Application No. PCT/JP2011/005590 dated Dec. 13, 2011, and English translation thereof (2 pages).

Office Action in corresponding Chinese application No. 201180049002.4 dated Jan. 13, 2014 (8 pages).

Office Action issued in Korean Patent Application No. 10-2013-7007966, dated Apr. 28, 2014 (14 pages).

Extended European Search Report issued in corresponding European Application No. 11832264.3 dated Oct. 18, 2016 (10 pages).

"Cellular Attachment to Ultraviolet Ozone Modified Polystyrene Surfaces," Teare D.O. et al., American Chemical Society Langmuir., vol. 16, pp. 2818-2824, Jan. 21, 2000 (7 pages).

"Line Energy and the Relation Between Advancing, Receding, and Young Contact Angles", Tadmor R., American Chemical Society Langmuir., vol. 20, pp. 7659-7664, Jul. 30, 2004(6 pages).

"Guide to Use Plastic Additives," Kogyo Chosakai Publishing Co., 1st edition, 2nd impression, pp. 61-67, Feb. 15, 1998 (8 pages).

* cited by examiner

FIG.1A
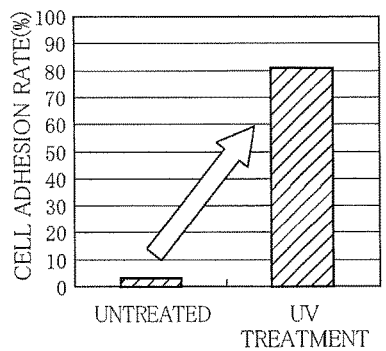
FIG.1B
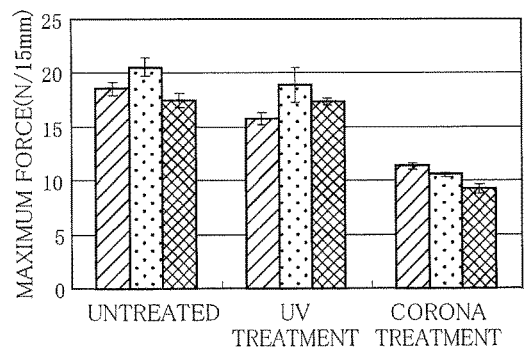
FIG.2
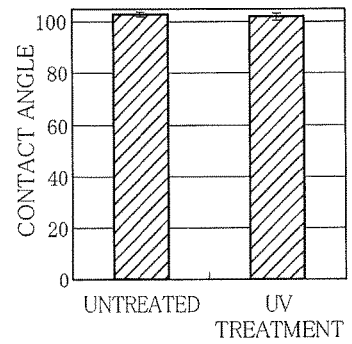
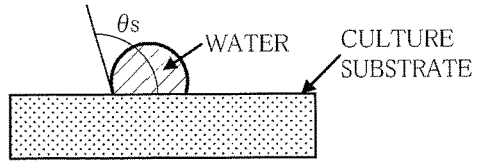
FIG.3
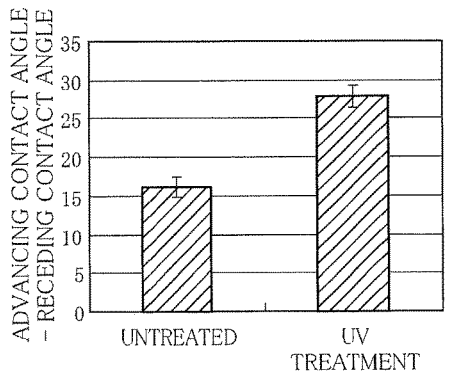
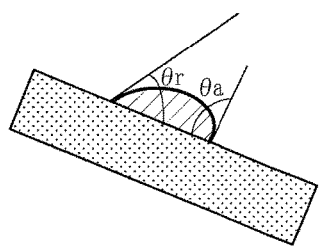

FIG. 8

| | Resin | Resin (inner surface) | Manufacturer | Acid protection | Film-forming method | Treatment | Cell adhesion rate (%) | Initial number of cells (cells/spot) | Culture time (hr) | Contact angle (°) | Hysteresis (°) | Heat-seal strength (N/15 mm) |
|---|---|---|---|---|---|---|---|---|---|---|---|---|
| Example 1 | EPPE | Excellen FX CX3007 | Sumitomo Chemical | Yes | Extrusion | UV after forming bag | 80.8 | 7.8x10⁻⁴ | 28 | 101.9 | 27.8 | 15.8 |
| Example 2 | EPPE | Excellen FX CX3502 | Sumitomo Chemical | Yes | Extrusion | UV after forming bag | 87.5 | 7.8x10⁻⁴ | 28 | 103.8 | 35.9 | 18.9 |
| Example 3 | EPPE | Excellen GMH CB2001 | Sumitomo Chemical | Yes | Extrusion | UV after forming bag | 86.1 | 7.8x10⁻⁴ | 28 | 100.0 | 26.5 | - |
| Example 4 | LLDPE | Kernel KS240T | Japan Polyethylene | Yes | Extrusion | UV after forming bag | 82.0 | 7.8x10⁻⁴ | 28 | 105.7 | 35.0 | - |
| Example 5 | LLDPE | Kernel KS340T | Japan Polyethylene | Yes | Extrusion | UV after forming bag | 87.1 | 7.8x10⁻⁴ | 28 | 104.3 | 40.9 | 17.3 |
| Example 6 | LLDPE | Kernel KF283 | Japan Polyethylene | Yes | Extrusion | UV after forming bag | 81.0 | 8.9x10⁻⁴ | 28 | 95.6 | 30.0 | - |
| Example 7 | PP | Novatec-PP MG3F | Japan Polypropylene | Yes | Hot pressing | Direct UV | 82.7 | 7.2x10⁻⁴ | 24 | 97.3 | 25.9 | - |
| Example 8 | EPPE | Excellen FX CX3007 | Sumitomo Chemical | Yes | Hot pressing | preUV | 91.9 | 7.2x10⁻⁴ | 24 | 102.2 | 29.2 | - |
| Comparative Example 1 | EPPE | Excellen FX CX3007 | Sumitomo Chemical | Yes | Extrusion | No | 3.2 | 7.8x10⁻⁴ | 28 | 102.7 | 16.1 | 18.5 |
| Comparative Example 2 | EPPE | Excellen FX CX3502 | Sumitomo Chemical | Yes | Extrusion | No | 1.9 | 7.8x10⁻⁴ | 28 | 103.2 | 17.0 | 20.5 |
| Comparative Example 3 | EPPE | Excellen GMH CB2001 | Sumitomo Chemical | Yes | Extrusion | No | 20.7 | 7.8x10⁻⁴ | 28 | 100.1 | 17.8 | - |
| Comparative Example 4 | EPPE | Excellen GMH CB5002 | Sumitomo Chemical | No | Extrusion | No | 18.6 | 7.8x10⁻⁴ | 28 | 101.0 | 15.6 | - |
| Comparative Example 5 | EPPE | Excellen GMH CB5002 | Sumitomo Chemical | No | Extrusion | UV after forming bag | 12.5 | 7.8x10⁻⁴ | 28 | 100.4 | 17.1 | - |
| Comparative Example 6 | LLDPE | Kernel KS240T | Japan Polyethylene | Yes | Extrusion | No | 13.5 | 7.8x10⁻⁴ | 28 | 106.0 | 21.9 | - |
| Comparative Example 7 | LLDPE | Kernel KS340T | Japan Polyethylene | Yes | Extrusion | No | 17.6 | 7.8x10⁻⁴ | 28 | 103.6 | 25.0 | 17.5 |
| Comparative Example 8 | LLDPE | Kernel KF283 | Japan Polyethylene | Yes | Extrusion | No | 39.0 | 8.9x10⁻⁴ | 28 | 96.8 | 15.0 | - |
| Comparative Example 9 | LLDPE | Kernel KM262 | Japan Polyethylene | No | Extrusion | No | 16.0 | 7.8x10⁻⁴ | 28 | 100.9 | 15.6 | - |
| Comparative Example 10 | LLDPE | Kernel KM262 | Japan Polyethylene | No | Extrusion | UV after forming bag | 17.3 | 7.8x10⁻⁴ | 28 | 100.8 | 16.2 | - |
| Comparative Example 11 | LDPE | UBE Polyethylene L719 | Ube-Maruzen Polyethylene | No | Extrusion | No | 53.0 | 8.9x10⁻⁴ | 28 | 102.4 | 15.0 | - |
| Comparative Example 12 | LDPE | UBE Polyethylene L719 | Ube-Maruzen Polyethylene | No | Extrusion | UV after forming bag | 47.9 | 8.9x10⁻⁴ | 28 | 102.3 | 17.8 | - |
| Comparative Example 13 | PP | Novatec-PP MG3F | Japan Polypropylene | Yes | Hot pressing | No | 21.1 | 7.2x10⁻⁴ | 24 | 99.5 | 16.1 | - |
| Comparative Example 14 | EPPE | Excellen FX CX3007 | Sumitomo Chemical | Yes | Extrusion | Corona treatment | - | - | - | 87.6 | - | 11.3 |
| Comparative Example 15 | EPPE | Excellen FX CX3502 | Sumitomo Chemical | Yes | Extrusion | Corona treatment | - | - | - | 91.5 | - | 10.6 |
| Comparative Example 16 | LLDPE | Kernel KS340T | Japan Polyethylene | Yes | Extrusion | Corona treatment | - | - | - | 85.8 | - | 9.2 |

CULTURE CONTAINER FOR ADHERENT CELLS AND METHOD FOR PRODUCING CULTURE CONTAINER FOR ADHERENT CELLS

TECHNICAL FIELD

The invention relates to a cell culture technique. In particular, the invention relates to an adherent cell culture vessel for culturing adherent cells that require a vessel wall or the like as a scaffold during culture, and a method for producing an adherent cell culture vessel.

BACKGROUND ART

In recent years, it has been desired to efficiently culture a large amount of cells, tissue, microorganisms, or the like in an artificial environment in the fields of drug production, gene therapy, regenerative medicine, immunotherapy, and the like.

A culture vessel (culture bag) may be charged with cells and a culture medium, and the cells may be automatically cultured in large quantities in the closed system.

Such a culture vessel is required to exhibit gas permeability and durability necessary for cell culture, heat-seal strength necessary for forming a bag, and the like, and has been formed using a polyolefin resin that exhibits these properties.

When using a culture vessel that is formed of a polyolefin resin, floating cells can be easily cultured, but it has been difficult to efficiently culture adherent cells that require a vessel wall or the like as a scaffold during culture. Specifically, it is necessary for the culture surface to have moderate wettability and hydrophilicity in order to allow adherent cells to adhere to the wall of the culture vessel. However, since the surface of a culture vessel formed of a polyolefin resin is hydrophobic, adherent cells cannot sufficiently adhere to the culture surface, and it has been difficult to achieve high proliferation efficiency.

In order to solve the above problem, a technique that subjects the culture surface of a film that forms a culture vessel to a hydrophilization treatment using a corona discharge method (see Patent Document 1) or a UV-ozone method (see Patent Documents 2 and 3) before forming a culture vessel in the shape of a bag has been proposed.

Patent Document 1: JP-A-6-98756
Patent Document 2: JP-A-2009-27944
Patent Document 3: JP-A-2009-27945

SUMMARY OF THE INVENTION

Technical Problem

However, since the heat-seal strength of the film significantly decreases as a result of performing the hydrophilization treatment, it may be difficult to appropriately form a culture vessel in the shape of a bag.

In order to solve the above problem, Patent Document 3 proposes performing the UV-ozone treatment while masking the heat seal area of the film. However, this method requires a complex production step.

Since the culture surface is exposed during the hydrophilization treatment, it has been difficult to produce a culture vessel in a sterile manner. Therefore, a highly clean production environment may be required.

The inventors of the invention conducted extensive studies, and found that the adhesion rate of adherent cells to the culture surface in a state in which a culture medium is contained in the culture vessel can be significantly improved without hydrophilizing the culture surface by applying specific UV rays to a resin that forms the culture vessel. This finding has led to the completion of the invention.

An object of the invention is to provide an adherent cell culture vessel that ensures that the cell adhesion rate can be improved, and adherent cells can be easily cultured by increasing the hysteresis (advancing contact angle-receding contact angle when water runs down) to be larger than a given value while ensuring that part or the entirety of the inner surface of the culture vessel formed of a polyolefin has a high static water contact angle (i.e., exhibits hydrophobicity), and a method for producing an adherent cell culture vessel.

Solution to Problem

An adherent cell culture vessel according to one aspect of the invention includes a single-layer or multi-layer film or sheet that includes a layer of a polyolefin as at least an innermost layer, part or entirety of an inner surface of the culture vessel having a static water contact angle of 95° or more, and having an advancing contact angle and a receding contact angle that satisfy the following expression (1) when water runs down along the inner surface of the culture vessel.

A method for producing an adherent cell culture vessel according to another aspect of the invention includes applying UV rays having a wavelength other than an ozone-generating wavelength to a single-layer or multi-layer film or sheet that includes a layer of a polyolefin as at least an innermost layer so that part or entirety of an inner surface of a culture vessel formed of the film or sheet has a static water contact angle of 95° or more, and has an advancing contact angle and a receding contact angle that satisfy the following expression (1) when water runs down along the inner surface of the culture vessel.

A method for producing an adherent cell culture vessel according to another aspect of the invention includes applying UV rays having a wavelength other than an ozone-generating wavelength to pellets of a polyolefin, forming a single-layer or multi-layer film or sheet that includes a layer of the polyolefin as at least an innermost layer, and forming an adherent cell culture vessel using the film or sheet so that part or entirety of an inner surface of the culture vessel has a static water contact angle of 95° or more, and has an advancing contact angle and a receding contact angle that satisfy the following expression (1) when water runs down along the inner surface of the culture vessel.

$$\text{Advancing contact angle} - \text{receding contact angle} > 25° \quad (1)$$

Advantageous Effects of the Invention

These aspects of the invention make it possible to produce a culture vessel that ensures that adherent cells can be efficiently cultured, without requiring a highly clean production environment and a complex production step such as a masking step.

BRIEF DESCRIPTION OF DRAWINGS

FIGS. 1A and 1B are views showing an improvement in cell adhesion rate and suppression of a decrease in heat-seal strength achieved by an adherent cell culture vessel according to the invention.

FIG. 2 is a view showing a change in properties (contact angle) of a film that forms an adherent cell culture vessel due to a UV irradiation treatment.

FIG. 3 is a view showing a change in properties (hysteresis) of a film that forms an adherent cell culture vessel due to a UV irradiation treatment.

FIG. 8 is a view showing the experimental conditions, the cell adhesion rate, the hysteresis, and the heat-seal strength in the examples and comparative examples.

DESCRIPTION OF EMBODIMENTS

Figure 4:
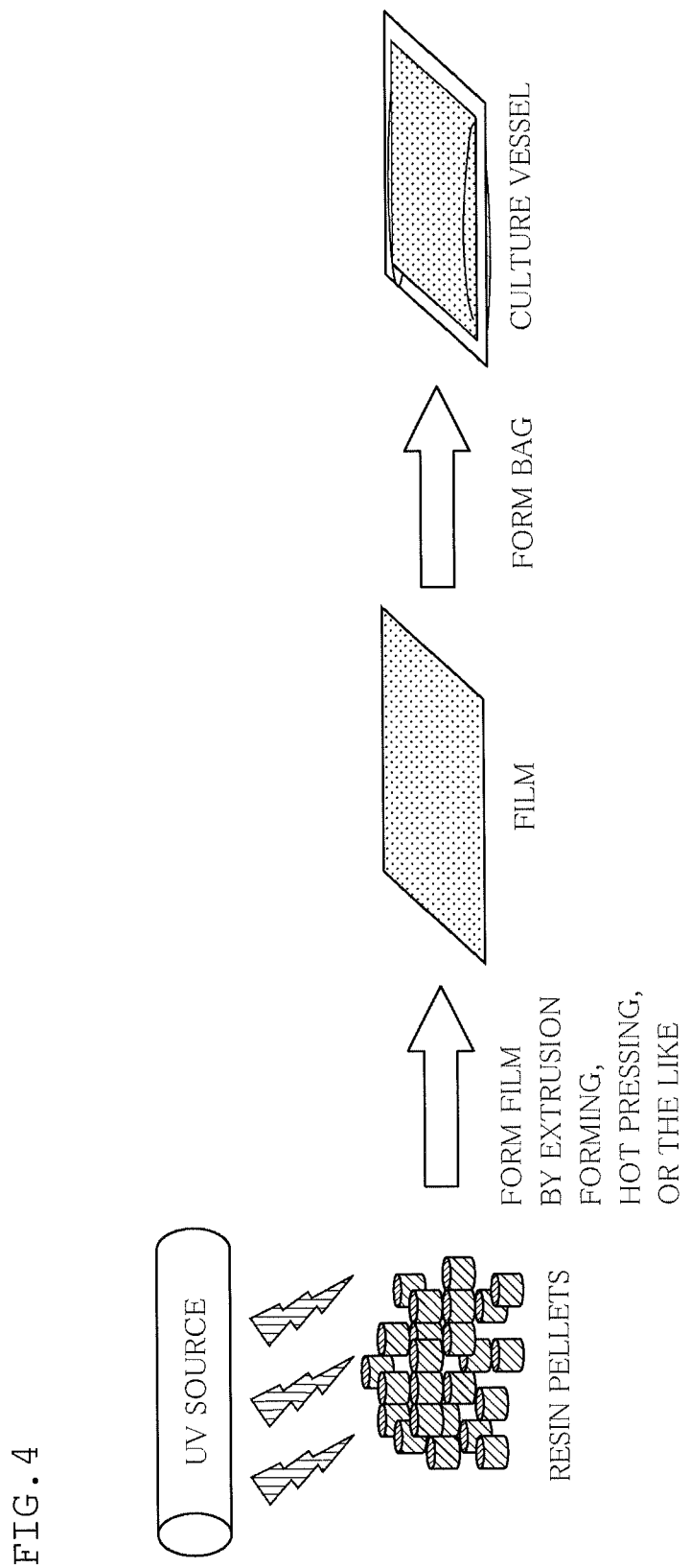
FIG. 4 is a view showing a process for producing an adherent cell culture vessel according to the invention.

An adherent cell culture vessel and a method for producing an adherent cell culture vessel according to several embodiments of the invention are described in detail below.

Culture Vessel

1. Material

An adherent cell culture vessel according to one embodiment of the invention is produced by forming a film using a flexible packaging material, and forming a bag using the film. The culture vessel is charged with a culture medium and cells, and the cells are cultured in the culture vessel. The culture vessel may be pressed using a plate, or the cells cultured in the culture vessel may be micrographed at regular intervals, for example. Therefore, it is desired that a material for forming the culture vessel exhibit gas permeability and durability necessary for culturing the cells, exhibit high heat-seal strength, and also exhibit transparency that allows the contents of the culture vessel to be observed.

A polyolefin resin (e.g., polyethylene or polypropylene) may suitably be used as a material that meets such requirements.

The film may be a single-layer film, or may be a multi-layer film that includes two or more layers. A multi-layer film may be formed by stacking different polyolefin resins of different type or brand. The film includes a layer of a polyolefin as at least the innermost layer, and may include a layer formed of a resin other than a polyolefin. The film may be formed in the form of a sheet.

It is preferable that the material for forming the adherent cell culture vessel according to one embodiment of the invention include a polyolefin resin and an antioxidant. The hysteresis of the film that forms the adherent cell culture vessel can be increased by applying specific UV rays to the material that includes an antioxidant, and the hydrophilicity of the culture surface can be improved when the culture vessel is charged with a culture medium, so that adhesion of cells can be improved (described later).

The antioxidant is not particularly limited. It is preferable to use a phenol-based antioxidant or a phosphorus-based antioxidant due to low cytotoxicity and a capability to advantageously increase the hysteresis.

2. UV Irradiation Treatment

The properties of the film that forms the adherent cell culture vessel according to one embodiment of the invention are changed by applying specific UV rays to the polyolefin resin to modify the properties of the polyolefin resin.

The properties of the culture surface of the culture vessel can be changed by forming the culture vessel in the shape of a bag using the film formed of the polyolefin resin, and applying UV rays from the outer side of the culture vessel.

The culture surface does not show a significant change in contact angle (i.e., the culture surface is not hydrophilized) when UV rays are applied to the culture vessel (film) (described later).

On the other hand, the hysteresis (contact angle hysteresis) of the culture surface of the adherent cell culture vessel according to one embodiment of the invention increases as a result of applying specific UV rays. As a result, the culture surface exhibits high hydrophilicity when the culture vessel is charged with a culture medium, and the cell adhesion rate is improved.

In one embodiment of the invention, a UV source that does not apply light having an ozone-generating wavelength (185 nm) is used for the UV irradiation treatment. For example, a low-pressure mercury lamp that has a dominant wavelength of 254 nm and can cut the ozone-generating wavelength using a quartz tube or the like may suitably be used.

The adherent cell culture vessel according to one embodiment of the invention is thus configured so that the cell adhesion rate can be improved without causing the culture surface to show a significant change in contact angle by applying UV rays having a wavelength other than the ozone-generating wavelength to the polyolefin resin.

Specifically, the adherent cell culture vessel according to one embodiment of the invention can be produced without exposing the culture surface since the culture surface is not hydrophilized.

Moreover, the film shows only a small decrease in heat-seal strength. Therefore, the culture vessel can be successfully produced even if UV rays are applied to the film before forming the culture vessel (bag) using the film.

In contrast, the UV-ozone method disclosed in Patent Document 2 hydrophilizes the culture surface by applying UV rays having the ozone-generating wavelength (i.e., the contact angle decreased from 104° to 71° in the examples of Patent Document 2). It is considered that ozone derived from oxygen in air reacts directly with the surface of the material, and the culture surface is hydrophilized by applying UV rays having the ozone-generating wavelength. In Patent Document 2, a resin that is easily hydrophilized, ensures hydrophilization stability, and has a high glass transition temperature is used as the vessel material. Since the molecular chain of such a material does not move at room temperature, it is difficult for a hydrophilic group to enter the resin after the surface has been hydrophilized, so that hydrophilization stability is obtained.

The adherent cell culture vessel according to one embodiment of the invention is formed using polyethylene or polypropylene. Since the molecular chain of polyethylene or polypropylene can move at room temperature, and thermodynamic stability is obtained in air when a hydrophilic group is present inside the resin rather than the surface of the resin, a hydrophilic functional group rarely moves to the surface of the resin when the amount of hydrophilic functional group is small. Therefore, the surface of the resin is hydrophilized to only a small extent.

3. Cell Adhesion Rate

The inner surface of the adherent cell culture vessel according to one embodiment of the invention shows a remarkably improved cell adhesion rate. FIG. 1A shows the cell adhesion rate of the adherent cell culture vessel according to one embodiment of the invention that was subjected to the UV irradiation treatment (Example 1), and the cell adhesion rate of a culture vessel that was produced in the same manner as the adherent cell culture vessel according to one embodiment of the invention, except that the UV irradiation treatment was not performed (Comparative Example 1). The cell adhesion rate refers to the ratio (%) of the number of adhering cells to the total number of floating cells and adhering cells after the adherent cells have been cultured for 28 hours.

As shown in FIG. 1, the cell adhesion rate increased from 3.2% to 80.8% due to the UV irradiation treatment.

Since the cell adhesion rate can be remarkably improved using the adherent cell culture vessel according to one embodiment of the invention, the adherent cell culture efficiency can be significantly improved.

4. Heat-Seal Strength

The adherent cell culture vessel according to one embodiment of the invention can suppress a decrease in heat-seal strength that may occur as a result of improving the cell adhesion rate of the inner surface of the culture vessel.

FIG. 1B shows the heat-seal strength of the adherent cell culture vessel according to one embodiment of the invention that was subjected to the UV irradiation treatment, the heat-seal strength of a culture vessel that was produced in the same manner as the adherent cell culture vessel according to one embodiment of the invention, except that the UV irradiation treatment was not performed, and the heat-seal strength of a culture vessel that was produced in the same manner as the adherent cell culture vessel according to one embodiment of the invention, except that a corona discharge treatment was performed instead of the UV irradiation treatment. The heat-seal strength shown in FIG. 1 is based on the maximum force. FIG. 1B shows the heat-seal strength obtained in Examples 1, 2, and 5 ("UV treatment"), the heat-seal strength obtained in Comparative Examples 1, 2, and 7 ("Untreated"), and the heat-seal strength obtained in Comparative Examples 14, 15, and 16 ("Corona treatment").

As shown in FIG. 1, while the culture vessel subjected to the corona discharge treatment showed a significant decrease in heat-seal strength as compared with the untreated culture vessel, the adherent cell culture vessel according to one embodiment of the invention that was subjected to the UV irradiation treatment showed only a small decrease in heat-seal strength.

Since a decrease in heat-seal strength can be suppressed using the adherent cell culture vessel according to one embodiment of the invention, the adherent cell culture vessel can be appropriately produced even if the UV irradiation treatment is performed before forming the culture vessel (bag).

5. Contact Angle

The contact angle of the culture surface is described below with reference to FIG. 2. The hydrophilicity of the culture surface of a cell culture vessel has a correlation with the contact angle of the culture surface. The term "contact angle" used herein refers to an angle (static water contact angle) formed by a liquid surface and a solid surface when a stationary liquid comes in contact with a solid surface ($\theta s$ in FIG. 2). The solid surface has high hydrophobicity when the contact angle is large, and has high hydrophilicity when the contact angle is small.

It is generally considered that the contact angle of the culture surface suitable for culturing adherent cells is about 60 to 80° (Journal of Biomedical Materials Research, Vol. 28, 783-789 (1994)). When the contact angle is within the above range, the culture surface has high hydrophilicity, and adherent cells easily adhere to the culture surface.

FIG. 2 shows the contact angle of the adherent cell culture vessel according to one embodiment of the invention that was subjected to the UV irradiation treatment (Example 1 (101.9±1.7°)), and the contact angle of a culture vessel that was produced in the same manner as the adherent cell culture vessel according to one embodiment of the invention, except that the UV irradiation treatment was not performed (Comparative Example 1 (102.7±1°)).

Specifically, the contact angle of the culture surface changed to only a small extent (i.e., the culture surface was not hydrophilized) due to the UV irradiation treatment.

Therefore, the adherent cell culture vessel according to one embodiment of the invention shows a small decrease in heat-seal strength in spite of the UV irradiation treatment.

When using a related-art technique, adherent cells cannot sufficiently adhere to the culture surface when the culture surface is not hydrophilized. In contrast, the adhesion rate of adherent cells to the culture surface can be improved by the adherent cell culture vessel according to one embodiment of the invention without hydrophilizing the culture surface.

The contact angle of the adherent cell culture vessel according to one embodiment of the invention is preferably 95° or more. If the contact angle of the adherent cell culture vessel is less than 95°, the hydrophilicity of the culture surface may increase, and the heat-seal strength may significantly decrease.

Since part or the entirety of the inner surface of the adherent cell culture vessel according to one embodiment of the invention subjected to the UV irradiation treatment has a contact angle of 95° or more, a decrease in heat-seal strength can be suppressed.

6. Hysteresis

The hysteresis of the film that forms the cell culture vessel can be increased by the UV irradiation treatment. The term "hysteresis" used herein refers to a contact angle hysteresis that indicates the difference between the advancing contact angle ($\theta a$) and the receding contact angle ($\theta r$) (run-down hysteresis ($\theta a - \theta r$)) when a water droplet runs down along the culture surface. Specifically, a water droplet is dropped onto a surface that is supported horizontally, and the surface is gradually tilted. The hysteresis is calculated based on the advancing contact angle and the receding contact angle at the time when the water droplet starts to run down along the surface. The hysteresis is used as an index that indicates the dynamic wettability of a surface.

FIG. 3 shows the hysteresis of the adherent cell culture vessel according to one embodiment of the invention that was subjected to the UV irradiation treatment (Example 1 (27.8°)), and the hysteresis of a culture vessel that was produced in the same manner as the adherent cell culture vessel according to one embodiment of the invention, except that the UV irradiation treatment was not performed (Comparative Example 1 (16.1°).

Specifically, the hysteresis of the culture surface significantly increased (i.e., the dynamic wettability of the culture surface increased) due to the UV irradiation treatment.

Since the culture surface of the adherent cell culture vessel according to one embodiment of the invention exhibits high dynamic wettability due to the UV irradiation treatment although the culture surface is not hydrophilized, the cell adhesion rate can be improved.

It is preferable that the advancing contact angle and the receding contact angle when a water droplet runs down along the culture surface of the adherent cell culture vessel according to one embodiment of the invention satisfy the following expression (1).

$$\text{Advancing contact angle} - \text{receding contact angle} > 25° \quad (1)$$

As is clear from the examples, while a sufficient cell adhesion rate cannot be obtained when the hysteresis is 25° or less, the cell adhesion rate is significantly improved when the hysteresis is larger than 25°.

The entire adherent cell culture vessel may have a hysteresis of larger than 25°, or only part or the entirety of the inner surface of the adherent cell culture vessel may have a hysteresis of larger than 25°. Even when only part of the inner surface of the adherent cell culture vessel has a hysteresis of larger than 25°, the cell adhesion rate can be improved in the part of the inner surface of the adherent cell culture vessel, so that the cell proliferation efficiency can be improved.

Method for Producing Adherent Cell Culture Vessel

The adherent cell culture vessel according to one embodiment of the invention may be produced by a normal method, except that a polyolefin resin is used as the material, and UV rays having a wavelength other than the ozone-generating wavelength are applied. For example, the adherent cell culture vessel according to one embodiment of the invention may be produced by the following steps (see FIG. 4).

A film (or sheet) is formed by extrusion molding or hot pressing using polyolefin resin pellets.

It is preferable to add a phenol-based antioxidant or a phosphorus-based antioxidant to the polyolefin resin when producing the resin pellets. When the antioxidant is added to the polyolefin resin, the hysteresis of the polyolefin resin can be advantageously increased by performing the UV irradiation treatment.

A bag is then formed using the film to obtain an adherent cell culture vessel.

Figure 5A:
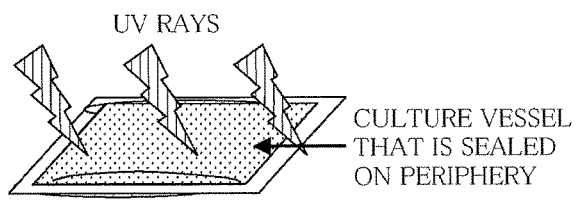
FIGS. 5A, 5B, and 5C are views showing the UV irradiation target (film, culture vessel, or film during formation) when producing an adherent cell culture vessel according to the invention.

The UV irradiation treatment may be performed after forming a bag using the film to obtain a culture vessel (see FIG. 5A). Specifically, since the UV irradiation treatment is not performed to hydrophilize the culture surface, UV rays need not be applied directly to the culture surface. The hysteresis of the culture surface can be increased by applying UV rays from the outside of the closed area formed by the film or sheet. It is also possible to ensure sterility of the culture surface by applying UV rays from the outside of the closed area.

Figure 5B:
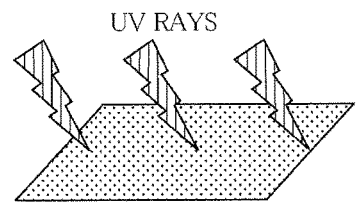
Figure 5C:
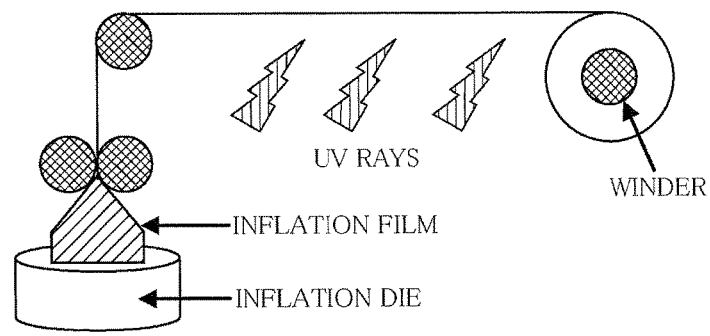

The UV irradiation treatment may also be performed on a film or sheet that is not formed in the shape of a bag (see FIG. 5B). The UV irradiation treatment may also be performed when winding a film from an inflation film (see FIG. 5C). The UV irradiation treatment may also be performed on the resin pellets (see FIG. 4).

Specifically, since UV rays having a wavelength other than the ozone-generating wavelength are applied to the film, the surface of the film is not hydrophilized, and a significant decrease in heat-seal strength of the film does not occur.

Therefore, a bag can be appropriately formed even if the UV irradiation treatment is performed on the film or sheet before forming a bag, and the adherent cell culture vessel can be produced without performing a complex step that masks the heat seal area.

Adhesion Mechanism

A mechanism by which adherent cells adhere to the adherent cell culture vessel according to one embodiment of the invention is described below.

Adherent cells normally adhere to a substrate such as a culture vessel as described below.

Specifically, adherent proteins (e.g., fibronectin or vitronectin) contained in a culture medium are adsorbed on the substrate. Integrin or the like that is present on the surface of the adherent cells interacts with and adheres to the adherent proteins. The adherent cells thus adhere to the substrate, and grow.

When the substrate is hydrophobic, the part of the adherent proteins to which the cells adhere interacts with the surface of the substrate, and interaction with the cells is inhibited. When the surface of the substrate is highly hydrophilic, the adherent proteins are not adsorbed on the substrate, and the adherent cells cannot adhere to the substrate.

It is conjectured that the hysteresis of the culture surface of the adherent cell culture vessel increases due to the UV irradiation treatment without an accompanying change in contact angle, and the cell adhesion rate is improved for the following reasons.

Figure 6:
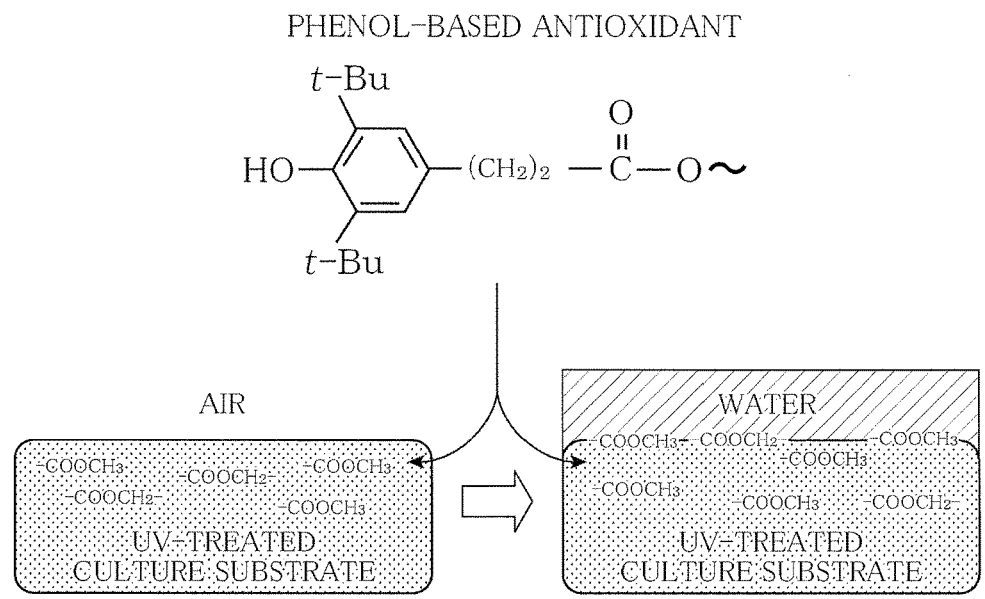
FIG. 6 is a view showing a cell adhesion mechanism when culturing cells using an adherent cell culture vessel according to the invention.

As illustrated in FIG. 6, ROO. is produced from the polyolefin resin that forms the adherent cell culture vessel according to one embodiment of the invention due to the UV irradiation treatment. ROO. reacts with the antioxidant contained in the polyolefin resin, so that the ester linkage site of the antioxidant that exhibits a higher degree of freedom can move due to the environment on the surface of the material.

Therefore, when the adherent cell culture vessel is charged with a culture medium, and the culture surface is wetted with water, the hydrophilic group is exposed on the culture surface, and attracts water. As a result, the hysteresis increases, and the cell adhesion rate is improved.

Since the hydrophilic group remains in the resin when the culture surface of the adherent cell culture vessel according to one embodiment of the invention comes in contact with air, the culture surface is hydrophobic, and the contact angle does not change.

According to the above adherent cell culture vessel and the method for producing the same, the contact angle and the hysteresis of the culture surface can be set within the specific ranges by applying UV rays having a wavelength other than the ozone-generating wavelength to the culture vessel that is formed of the polyolefin resin, and the cell adhesion rate can be improved without hydrophilizing the culture surface.

This makes it possible to provide an adherent cell culture vessel that achieves a high cell adhesion rate without requiring a highly clean production environment and a complex production step such as a masking step.

EXAMPLES

In the following examples and comparative examples, the performance and the properties of the adherent cell culture vessel according to the embodiments of the invention were evaluated as described below (see FIGS. 7 to 9).

1. The film-forming method, the UV irradiation method, the corona treatment method, 2. the cell adhesion performance evaluation method, 3. the contact angle measurement method, the hysteresis measurement method, and 4. the heat-seal strength measurement method employed in the examples and comparative examples are described below.

1. Film-Forming Method, UV Irradiation Method, and Corona Treatment Method

A film was extrusion-molded using a Labo Plastomill (manufactured by Toyo Seiki Seisaku-Sho, Ltd.). In some of the examples and comparative examples, a film was formed using a hot press (manufactured by Shoji Tekko Co., Ltd.).

The UV irradiation treatment was performed using a UV lamp ("TUV15W/G15T8" manufactured by Philips, dominant wavelength: 254 nm, the ozone-generating wavelength (185 nm) was cut off using a quartz tube). The UV irradiation treatment was performed at a cumulative dose of 5 J/cm$^2$ when performing the UV irradiation treatment on the bag or the film. In this case, UV rays were applied for 2 hours in a state in which the film was positioned apart from the lamp by 12 cm. The UV irradiation treatment was performed at a cumulative dose of 10 J/cm$^2$ when performing the UV irradiation treatment on the resin pellets. In this case, UV rays were applied for 2 hours in a state in which the resin pellets were positioned close to the lamp. The cumulative dose was measured using a cumulative UV meter "UIT-150" (manufactured by Ushio Inc.).

The corona treatment was performed using a high-frequency power supply "CG-102" (manufactured by Kasuga Electric Works Ltd.). The applied current was set to 3.5 A, the distance between the film and the electrode was set to 5 mm, and the film moving speed was set to 5 m/min.

2. Cell Adhesion Performance Evaluation Method

Adherent cells to be cultured were provided as described below.

Fetal bovine serum (manufactured by Invitrogen) was added to a medium "Nutrient mixture F/12 Ham" (manufactured by Sigma-Aldrich) in an amount of 10%. A CHO-K1 (Chinese hamster ovary) cell line was cultured on a cell culture dish (diameter: 6 cm, manufactured by Becton, Dickinson and Company). The resulting adherent cells were collected from the bottom, and the number of adherent cells was counted.

The film of each example or comparative example was attached to a Petri dish (diameter: 6 cm, manufactured by Becton, Dickinson and Company) in advance. The film subjected to the UV irradiation treatment after forming the bag was cut, and attached to the Petri dish.

A mixture (300 µl) of 150 µl of a fresh medium and 150 µl of the cell suspension collected from the bottom of the cell culture dish was seeded onto the film in a spot-like manner. The number of cells seeded onto the film differed depending on each example and comparative example since the number of cells collected differed depending on the experiment. The number of cells seeded onto the film was about 7.2 to 8.9×10$^4$ cells/spot. The culture area was 2 cm$^2$.

After 1 day had elapsed (after 24 or 28 hours had elapsed), the number of floating cells and the number of adhering cells were counted, and the cell adhesion rate was calculated using the following expression.

Cell adhesion rate=(number of adhering cells)/(number of floating cells+number of adhering cells)

3. Contact Angle Measurement Method and Hysteresis Measurement Method

The contact angle and the hysteresis were measured using a solid-liquid interface analysis system "DropMaster 700" (manufactured by Kyowa Interface Science Co., Ltd.).

Figure 7:
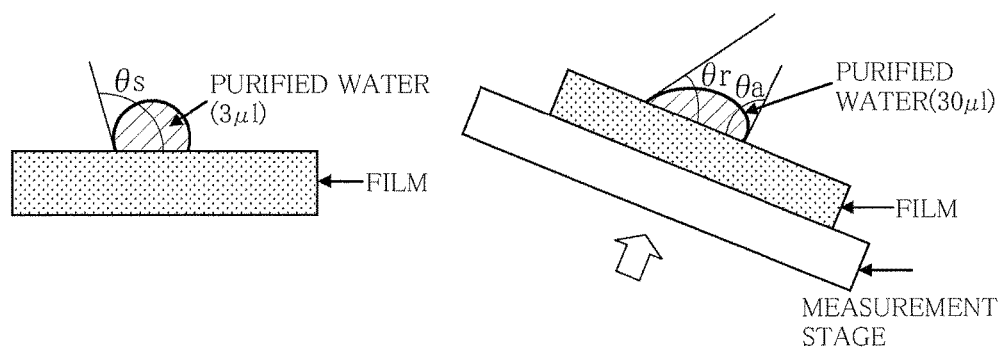
FIG. 7 is a view showing a contact angle measurement method and a hysteresis measurement method used in the examples and comparative examples.

As illustrated in FIG. 7, 3 µl of purified water was dropped onto the film, and the contact angle ($\theta$s) was measured. The run-down hysteresis ($\theta$a−$\theta$r) was then measured as follows. 30 µl of purified water was dropped onto the film, and the measurement stage was tilted by 1° every second. The advancing contact angle ($\theta$a) and the receding contact angle ($\theta$r) when the water ran down were calculated by a tangent method to calculate the run-down hysteresis ($\theta$a−$\theta$r).

4. Heat-Seal Strength Measurement Method

The heat-seal strength was measured using a heat seal tester (manufactured by Tester Sangyo Co, Ltd.). The seal width was set to 10 mm, the pressure was set to 3 kgf/cm$^2$, and the seal time was set to 2 seconds. Only the upper seal bar was heated to 140° C.

A tensile test was performed using a precision universal tester "Autograph AG-1S" (manufactured by Shimadzu Corporation). The width of a test piece was set to be 15 mm, and the test piece was pulled in the M.D. direction at a speed of 300 mm/min. The heat-seal strength was measured by the maximum test strength (N/15 mm).

The examples and the comparative examples are described below with reference to FIG. 8. In FIG. 8, EPPE stands for easy processing polyethylene, LLDPE stands for linear low-density polyethylene, PP stands for polypropylene, and LDPE stands for low-density polyethylene.

"UV after forming bag" in the column "Treatment" means that UV rays having a wavelength of 254 nm were applied after forming a bag using the film, and sealing the four sides of the bag. In this case, the UV irradiation treatment was performed at a cumulative dose of 5 J/cm$^2$.

"Direct UV" in the column "Treatment" means that UV rays having a wavelength of 254 nm were applied in a state in which the film was exposed. In this case, the UV irradiation treatment was performed at a cumulative dose of 5 J/cm$^2$.

"preUV" in the column "Treatment" means that UV rays having a wavelength of 254 nm were applied to the resin pellets before forming the film. In this case, the UV irradiation treatment was performed at a cumulative dose of 10 J/cm$^2$.

"Corona treatment" in the column "Treatment" means that the corona treatment was performed using a high-frequency power supply "CG-102" (manufactured by Kasuga Electric Works Ltd.) in a state in which the applied current was set to 3.5 A, the distance between the film and the electrode was set to 5 mm, and the film moving speed was set to 5 m/min.

Example 1

A film that forms the inner layer of the cell culture vessel was formed by extrusion-molding a resin "Excellen FX CX3007" (EPPE, manufactured by Sumitomo Chemical Co., Ltd.) that contains an antioxidant. The outer layer was formed using a resin "Excellen GMH CB2001" (EPPE, manufactured by Sumitomo Chemical Co., Ltd.) to obtain a two-layer film.

After forming a bag using the film, the four sides of the bag were sealed, and UV rays having a wavelength of 254 nm were applied to the film.

The adherent cells (CHO-K1 (Chinese hamster ovary) cell line) provided as described above were seeded onto the resulting culture vessel, and cultured. The initial number of cells was 7.8×10$^4$ cells/spot, and the culture area was 2 cm$^2$.

After 28 hours had elapsed, the number of floating cells and the number of adhering cells were counted, and the cell adhesion rate was calculated. The cell adhesion rate thus calculated was 80.8%.

The contact angle and the hysteresis of the culture surface of the culture vessel, and the heat-seal strength were measured. The contact angle was 101.9°, the hysteresis was 27.8°, and the heat-seal strength was 15.8 N/15 mm.

Example 2

A film that forms the inner layer of the cell culture vessel was formed by extrusion-molding a resin "Excellen FX CX3502" (EPPE, manufactured by Sumitomo Chemical Co., Ltd.) that contains an antioxidant. Experiments were performed in the same manner as in Example 1, except for the above point. The cell adhesion rate was 87.5%, the contact angle was 103.8°, the hysteresis was 35.9°, and the heat-seal strength was 18.9 N/15 mm.

Example 3

A film that forms the inner layer of the cell culture vessel was formed by extrusion-molding a resin "Excellen GMH CB2001" (EPPE, manufactured by Sumitomo Chemical Co., Ltd.) that contains an antioxidant. The outer layer was formed using a resin "Kernel KS240T" (LLDPE, manufactured by Japan Polyethylene Corporation) to obtain a two-layer film. Experiments were performed in the same manner as in Example 1, except for the above point. Note that the heat-seal strength was not measured. The cell adhesion rate was 86.1%, the contact angle was 100.0°, and the hysteresis was 26.5°.

Example 4

A film that forms the inner layer of the cell culture vessel was formed by extrusion-molding a resin "Kernel KS240T" (LLDPE, manufactured by Japan Polyethylene Corporation) that contains an antioxidant. Experiments were performed in the same manner as in Example 1, except for the above point. Note that the heat-seal strength was not measured. The cell adhesion rate was 82.0%, the contact angle was 105.7°, and the hysteresis was 35.0°.

Example 5

A film that forms the inner layer of the cell culture vessel was formed by extrusion-molding a resin "Kernel KS340T" (LLDPE, manufactured by Japan Polyethylene Corporation) that contains an antioxidant. Experiments were performed in the same manner as in Example 1, except for the above point. The cell adhesion rate was 87.1%, the contact angle was 104.3°, the hysteresis was 40.9°, and the heat-seal strength was 17.3 N/15 mm.

Example 6

A film that forms the single-layer cell culture vessel was formed by extrusion-molding a resin "Kernel KF283" (LLDPE, manufactured by Japan Polyethylene Corporation) that contains an antioxidant. Experiments were performed in the same manner as in Example 1, except that the initial number of cells was $8.9 \times 10^4$ cells/spot. Note that the heat-seal strength was not measured. The cell adhesion rate was 81.0%, the contact angle was 95.6°, and the hysteresis was 30.0°.

Example 7

A film that forms the single-layer cell culture vessel was formed by hot pressing a resin "Novatec-PP MG3F" (PP, manufactured by Japan Polypropylene Corporation) that contains an antioxidant.

UV rays having a wavelength of 254 nm were applied in a state in which the film was exposed.

The adherent cells (CHO-K1 (Chinese hamster ovary) cell line) provided as described above were seeded onto the resulting culture vessel, and cultured. The initial number of cells was $7.2 \times 10^4$ cells/spot, and the culture area was 2 $cm^2$.

After 24 hours had elapsed, the number of floating cells and the number of adhering cells were counted, and the cell adhesion rate was calculated. The cell adhesion rate thus calculated was 82.7%.

The contact angle and the hysteresis of the culture surface of the culture vessel were measured. The contact angle was 97.3°, and the hysteresis was 25.9°.

Example 8

As the film that forms the single-layer cell culture, "Excellen FX CX3007" (EPPE, manufactured by Sumitomo Chemical Co., Ltd.) that contains an antioxidant was used. UV rays having a wavelength of 254 nm were applied to the resin pellets thereof. A film was formed by hot pressing using the pellets to obtain a culture vessel.

The cells were cultured in the same manner as in Example 7 using the resulting culture vessel, and the cell adhesion rate was calculated. The cell adhesion rate thus calculated was 91.9%.

The contact angle and the hysteresis of the culture surface of the culture vessel were measured. The contact angle was 102.2°, and the hysteresis was 29.2°.

Comparative Example 1

Experiments were performed in the same manner as in Example 1, except that the resin used in Example 1 was used to form the inner layer of the cell culture vessel, but the UV irradiation treatment was not performed. The cell adhesion rate was 3.2%, the contact angle was 102.7°, the hysteresis was 16.1°, and the heat-seal strength was 18.5 N/15 mm.

Comparative Example 2

Experiments were performed in the same manner as in Example 2, except that the resin used in Example 2 was used to form the inner layer of the cell culture vessel, but the UV irradiation treatment was not performed. The cell adhesion rate was 1.9%, the contact angle was 103.2°, the hysteresis was 17.0°, and the heat-seal strength was 20.5 N/15 mm.

Comparative Example 3

Experiments were performed in the same manner as in Example 3, except that the resin used in Example 3 was used to form the inner layer of the cell culture vessel, but the UV irradiation treatment was not performed. The cell adhesion rate was 20.7%, the contact angle was 100.1°, and the hysteresis was 17.8°.

Comparative Example 4

A film that forms the inner layer of the cell culture vessel was formed by extrusion-molding a resin "Excellen GMH CB5002" (EPPE, manufactured by Sumitomo Chemical Co., Ltd.) that does not contain an antioxidant. The outer layer was formed using a resin "Kernel KM262" (LLDPE, manufactured by Japan Polyethylene Corporation) to obtain a two-layer film.

Experiments were performed in the same manner as in Example 3, except that UV irradiation treatment was not performed. The cell adhesion rate was 18.6%, the contact angle was 101.0°, and the hysteresis was 15.6°.

Comparative Example 5

A film that forms the inner layer of the cell culture vessel was formed by extrusion-molding the resin used in Comparative Example 4. The outer layer was formed using the resin used in Comparative Example 4 to obtain a two-layer film.

After forming a bag using the film, the four sides of the bag were sealed, and UV rays having a wavelength of 254 nm were applied to the film. Experiments were performed in the same manner as in Comparative Example 4, except that UV irradiation treatment was performed as described above. The cell adhesion rate was 12.5%, the contact angle was 100.4°, and the hysteresis was 17.1°.

Comparative Example 6

Experiments were performed in the same manner as in Example 4, except that the resin used in Example 4 was used to form the inner layer of the cell culture vessel, but the UV irradiation treatment was not performed. The cell adhesion rate was 13.5%, the contact angle was 106.0°, and the hysteresis was 21.9°.

Comparative Example 7

Experiments were performed in the same manner as in Example 5, except that the resin used in Example 5 was used to form the inner layer of the cell culture vessel, but the UV irradiation treatment was not performed. The cell adhesion rate was 17.6%, the contact angle was 103.6°, the hysteresis was 25.0°, and the heat-seal strength was 17.5 N/15 mm.

Comparative Example 8

Experiments were performed in the same manner as in Example 6, except that the resin used in Example 6 was used to form the single-layer cell culture vessel, but the UV irradiation treatment was not performed. The cell adhesion rate was 39.0%, the contact angle was 96.8°, and the hysteresis was 15.0°.

Comparative Example 9

A film that forms the inner layer of the cell culture vessel was formed by extrusion-molding a resin "Kernel KM262" (LLDPE, manufactured by Japan Polyethylene Corporation) that does not contain an antioxidant. The outer layer was formed using a resin "Excellen GMH CB5002" (EPPE, manufactured by Sumitomo Chemical Co., Ltd.) to obtain a two-layer film.

Experiments were performed in the same manner as in Example 3, except that UV irradiation treatment was not performed. The cell adhesion rate was 16.0%, the contact angle was 100.9°, and the hysteresis was 15.6°.

Comparative Example 10

A film that forms the inner layer of the cell culture vessel was formed by extrusion-molding the resin used in Comparative Example 9. The outer layer was formed using the resin used in Comparative Example 9 to obtain a two-layer film.

After forming a bag using the film, the four sides of the bag were sealed, and UV rays having a wavelength of 254 nm were applied to the film. Experiments were performed in the same manner as in Comparative Example 9, except that UV irradiation treatment was performed as described above. The cell adhesion rate was 17.3%, the contact angle was 100.8°, and the hysteresis was 16.2°.

Comparative Example 11

A film that forms the single-layer cell culture vessel was formed by extrusion-molding a resin "UBE Polyethylene L719" (LDPE, manufactured by Ube-Maruzen Polyethylene Co., Ltd.) that does not contain an antioxidant.

Experiments were performed in the same manner as in Example 3, except that UV irradiation treatment was not performed. The cell adhesion rate was 53.0%, the contact angle was 102.4°, and the hysteresis was 15.0°.

Comparative Example 12

A film that forms the single-layer cell culture vessel was formed by extrusion-molding the resin used in Comparative Example 11.

After forming a bag using the film, the four sides of the film were sealed, and UV rays having a wavelength of 254 nm were applied to the film. Experiments were performed in the same manner as in Comparative Example 11, except that UV irradiation treatment was performed as described above. The cell adhesion rate was 47.9%, the contact angle was 102.3°, and the hysteresis was 17.8°.

Comparative Example 13

Experiments were performed in the same manner as in Example 7, except that the resin used in Example 7 was used to form the single-layer cell culture vessel, but the UV irradiation treatment was not performed. The cell adhesion rate was 21.1%, the contact angle was 99.5°, and the hysteresis was 16.1°.

Comparative Example 14

A film that forms the inner layer of the cell culture vessel was formed by extrusion-molding the resin used in Example 1. The outer layer was formed using the resin used in Example 1 to obtain a two-layer film.

The corona discharge treatment was performed in a state in which the film was exposed, and the contact angle and the heat-seal strength were measured. The contact angle was 87.6°, and the heat-seal strength was 11.3 N/15 mm.

Comparative Example 15

A film that forms the inner layer of the cell culture vessel was formed by extrusion-molding the resin used in Example 2. The outer layer was formed using the resin used in Example 2 to obtain a two-layer film.

The corona discharge treatment was performed in a state in which the film was exposed, and the contact angle and the heat-seal strength were measured. The contact angle was 91.5°, and the heat-seal strength was 10.6 N/15 mm.

Comparative Example 16

A film that forms the inner layer of the cell culture vessel was formed by extrusion-molding the resin used in Example 5. The outer layer was formed using the resin used in Example 5 to obtain a two-layer film.

The corona discharge treatment was performed in a state in which the film was exposed, and the contact angle and the heat-seal strength were measured. The contact angle was 85.8°, and the heat-seal strength was 9.2 N/15 mm.

Figure 9:
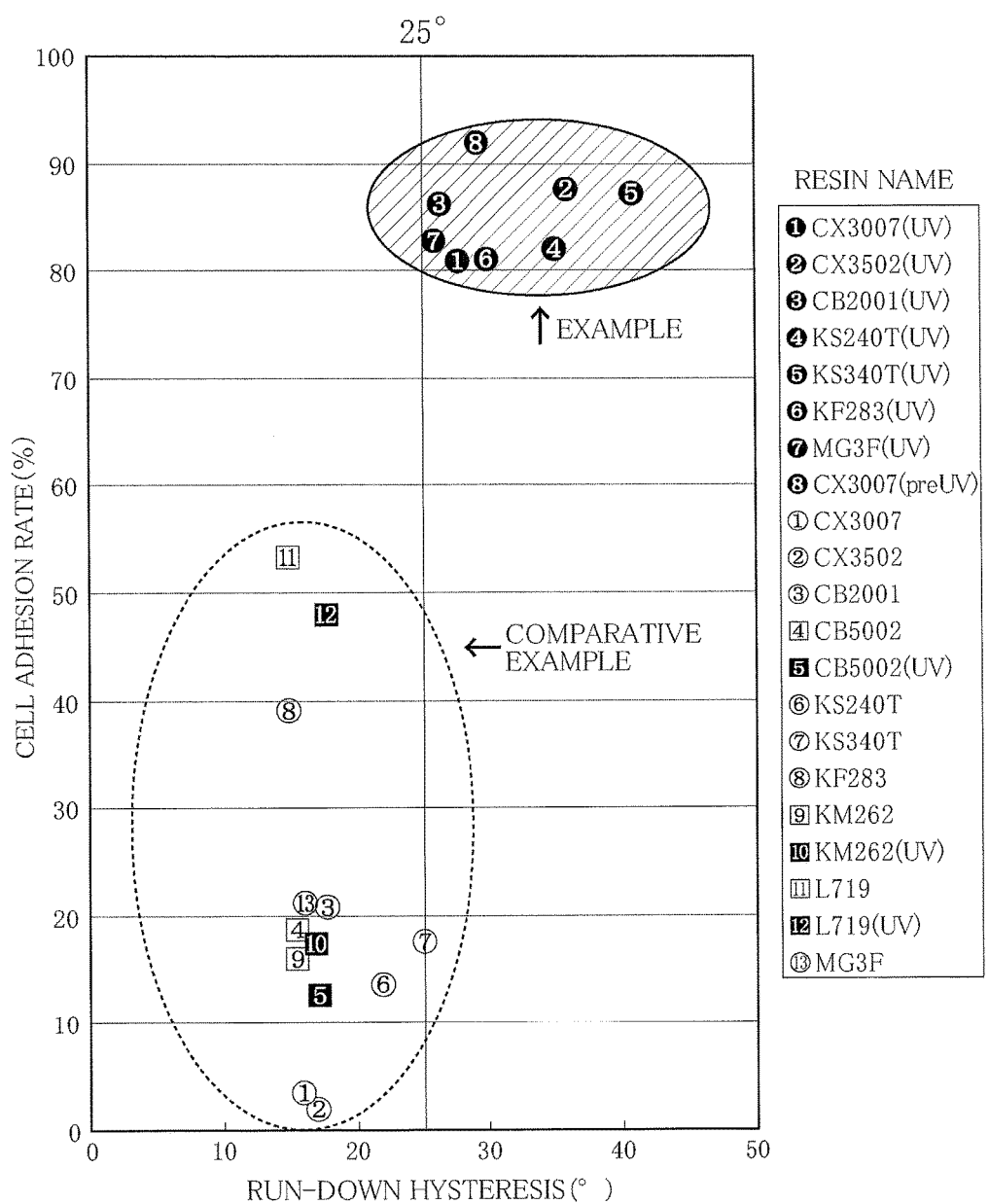
FIG. 9 is a view showing the relationship between the hysteresis and the cell adhesion rate in the examples and comparative examples.

FIG. 9 shows the relationship between the cell adhesion rate and the hysteresis in the examples and the comparative examples.

In FIG. 9, the black circles indicate the results for the culture vessels obtained in the examples in which the resin that contains an antioxidant was used, and UV rays having a wavelength of 254 nm were applied. The white circles indicate the results for the culture vessels obtained in the comparative examples in which the resin that contains an antioxidant was used, and UV rays were not applied. The black squares indicate the results for the culture vessels obtained in the comparative examples in which the resin that does not contain an antioxidant was used, and UV rays having a wavelength of 254 nm were applied. The white squares indicate the results for the culture vessels obtained in the comparative examples in which the resin that does not contain an antioxidant was used, and UV rays were not applied.

The contact angle of the inner surface of these culture vessels was 95° or more (i.e., the inner surface was not hydrophilized (see Examples 1 to 8 and Comparative Examples 1 to 13 in FIG. 8)).

The cell adhesion rate increased rapidly when the hysteresis exceeded 25°.

It was thus confirmed from the above results that it is preferable to produce an adherent cell culture vessel by utilizing a polyolefin resin (e.g., polyethylene or polypropylene) that contains an antioxidant, and applying UV rays having a wavelength other than the ozone-generating wavelength.

This makes it possible to produce a culture vessel that has a culture surface having a contact angle of 95° or more and a hysteresis of larger than 25°. A high cell adhesion rate can be achieved by culturing adherent cells using the culture vessel.

The invention is not limited to the above embodiments and examples. Various modifications may be made without departing from the scope of the invention.

Although the CHO-K1 cell line was used in the examples as the adherent cells, the adherent cells are not limited thereto. It is also possible to use other adherent cells. The type of the culture medium, the film-forming method, the bag-forming method, and the like may be appropriately changed. Although a low-pressure mercury lamp that emits UV rays having a wavelength other than the ozone-generating wavelength was used in the embodiments and the examples as the UV source, the UV source is not limited thereto as long as a culture surface having a contact angle of 95° or more and a hysteresis of larger than 25° can be formed. For example, a high-pressure mercury lamp that emits UV rays having a wavelength of 254 nm may also be used.

INDUSTRIAL APPLICABILITY

The invention may suitably be used when culturing a large amount of adherent cells using a cell culture vessel.

The invention claimed is:

1. An adherent cell culture vessel comprising: an inner layer,
wherein the inner layer is a layer of a polyolefin that forms an inner surface of the culture vessel,
wherein the polyolefin is selected from the group consisting of Easy Processing Polyethylene (EPPE), Linear Low-Density Polyethylene (LLDPE) and polypropylene (PP),
wherein the polyolefin comprises a phenol-based antioxidant comprising the following formula:

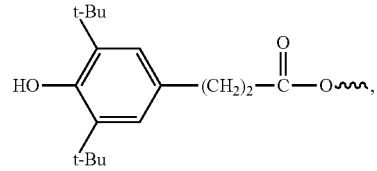

wherein the polyolefin is irradiated with UV rays including a wavelength of 254 nm at a cumulative dose of at least 5 J/cm$^2$, and
wherein a part or entirety of the inner surface of the culture vessel has a static water contact angle of 95° or more, and has an advancing contact angle and a receding contact angle that satisfy an expression (1) when water runs down along the inner surface of the culture vessel, Advancing contact angle−receding contact angle>25°  (1).

* * * * *